(12) United States Patent
Le Couedic et al.

(10) Patent No.: US 6,368,320 B1
(45) Date of Patent: Apr. 9, 2002

(54) CONNECTOR FOR BACKBONE OSTEOSYNTHESIS DEVICE

(75) Inventors: Régis Le Couedic, Pessac; Michel Lavergne, Merignac, both of (FR)

(73) Assignee: (DIMSO) Distribution Medicale du Sud-Ouest (FR)

( * ) Notice: Subject to any disclaimer, the term of this patent is extended or adjusted under 35 U.S.C. 154(b) by 0 days.

(21) Appl. No.: 09/581,104

(22) PCT Filed: Dec. 8, 1998

(86) PCT No.: PCT/FR98/02651

§ 371 Date: Aug. 17, 2000

§ 102(e) Date: Aug. 17, 2000

(87) PCT Pub. No.: WO99/29248

PCT Pub. Date: Jun. 17, 1999

(30) Foreign Application Priority Data

Dec. 9, 1997 (FR) ............................................. 97 15540

(51) Int. Cl.[7] .............................................. A61B 17/70
(52) U.S. Cl. ............................................ 606/61; 606/60
(58) Field of Search ...................................... 606/60, 61

(56) References Cited

U.S. PATENT DOCUMENTS

| | | | |
|---|---|---|---|
| 5,562,662 A | * | 10/1996 | Brumfield et al. ............. 606/61 |
| 5,645,544 A | * | 7/1997 | Tai et al. ....................... 606/61 |
| 5,702,393 A | | 12/1997 | Pfaifer .......................... 606/61 |
| 5,810,819 A | * | 9/1998 | Errico et al. ................... 606/61 |
| 5,984,928 A | * | 11/1999 | Hermann ....................... 606/72 |
| 5,997,539 A | * | 12/1999 | Errico et al. ................... 606/61 |
| 6,173,311 B1 | * | 1/2001 | Richelsoph ................... 606/61 |

FOREIGN PATENT DOCUMENTS

| | | | | |
|---|---|---|---|---|
| EP | 0786235 | * | 7/1997 | ................... 606/61 |
| EP | 0 813 845 A1 | | 12/1997 | |

* cited by examiner

Primary Examiner—Jeffrey A. Smith
Assistant Examiner—Michael B. Priddy
(74) Attorney, Agent, or Firm—Lerner, David, Littenberg, Krumholz & Mentlik, LLP

(57) ABSTRACT

An osteosynthesis device comprising first and second rods, a threaded member, and a connector having two jaws adapted to clamp onto the first rod, the connector having a threaded face and a housing extending between the jaws and the threaded face and adapted to receive the second rod bearing against the jaws, the connector being arranged so that a force (T) applied by the threaded member co-operating with the threaded face, against the second rod received in the housing towards the jaws urges the jaws towards each other so as to clamp onto the first rod. The connector is made as a single piece.

15 Claims, 3 Drawing Sheets

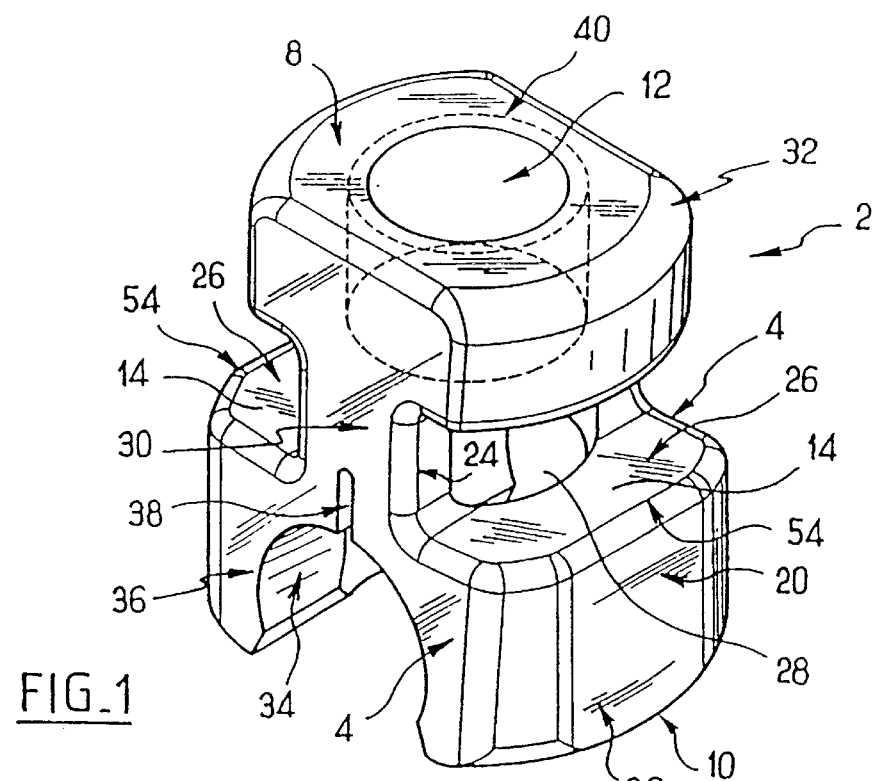
FIG_1
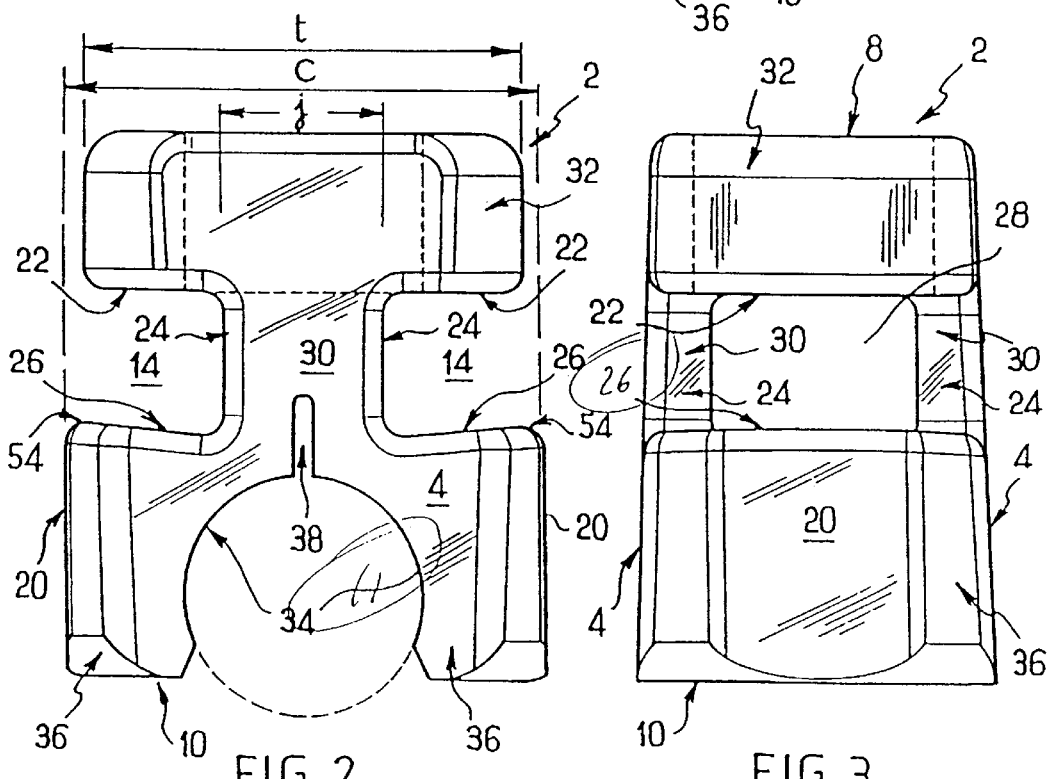
FIG_2   FIG_3

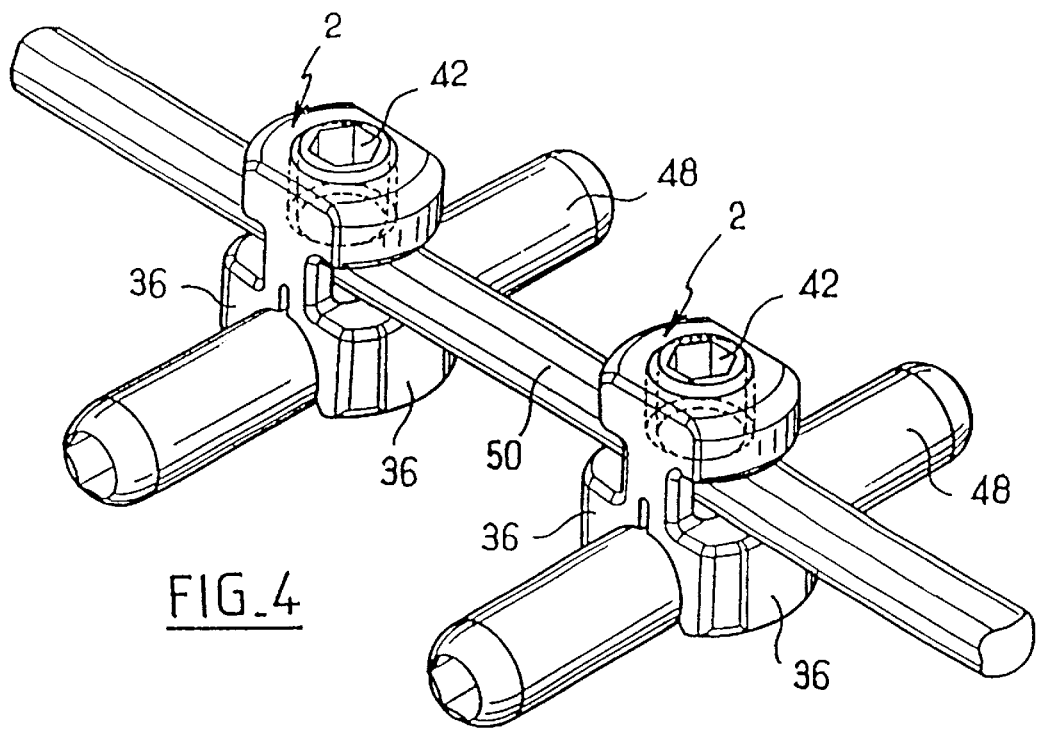
FIG_4
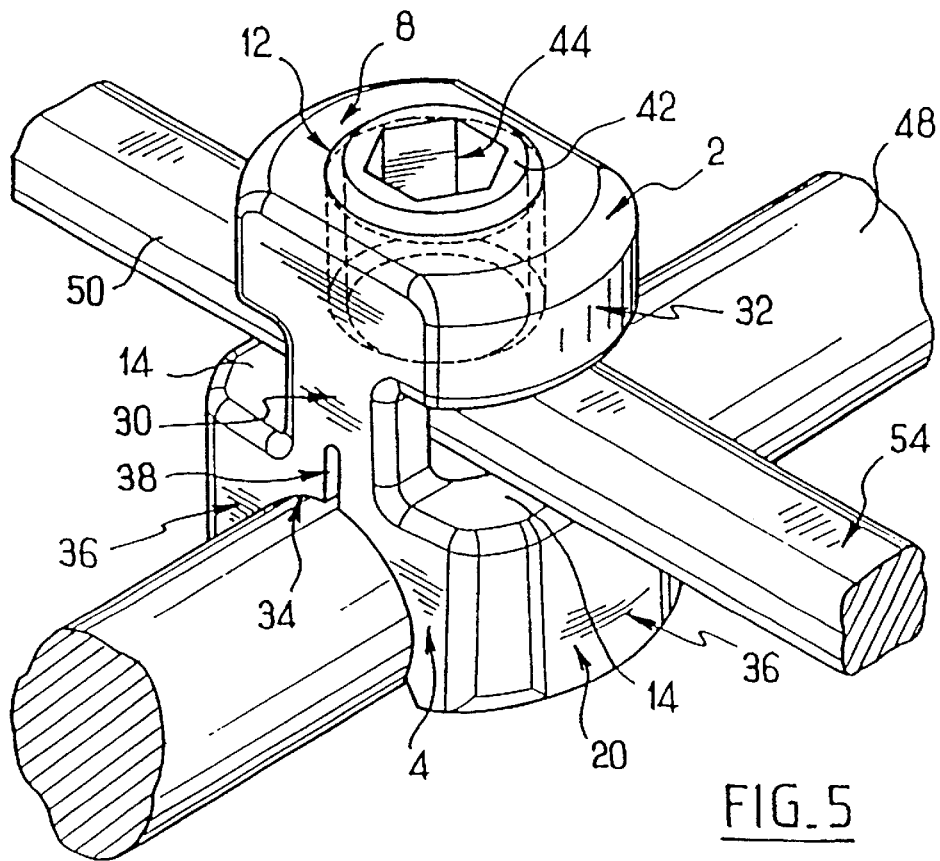
FIG_5

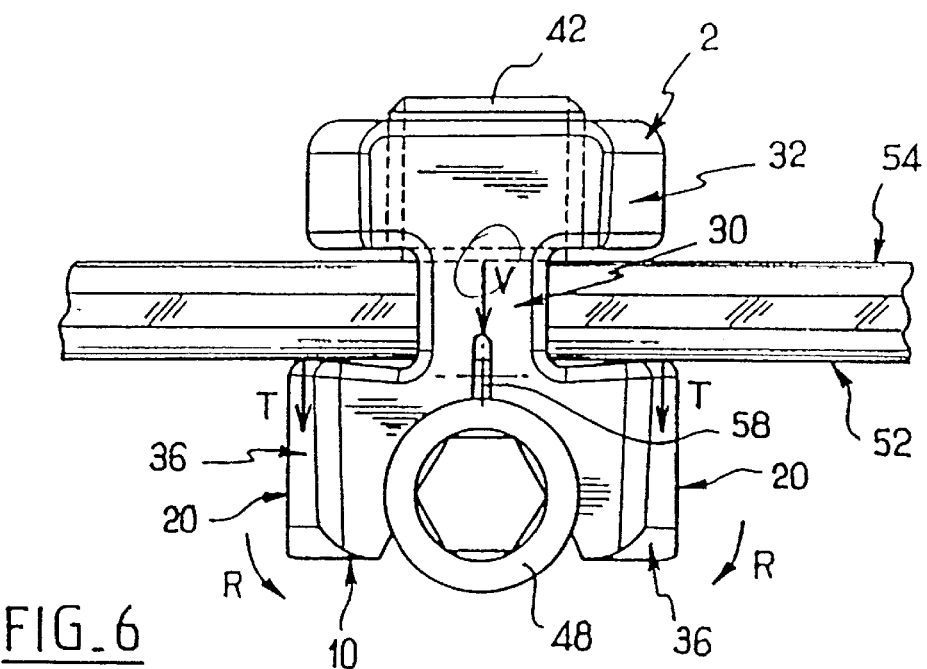
FIG_6
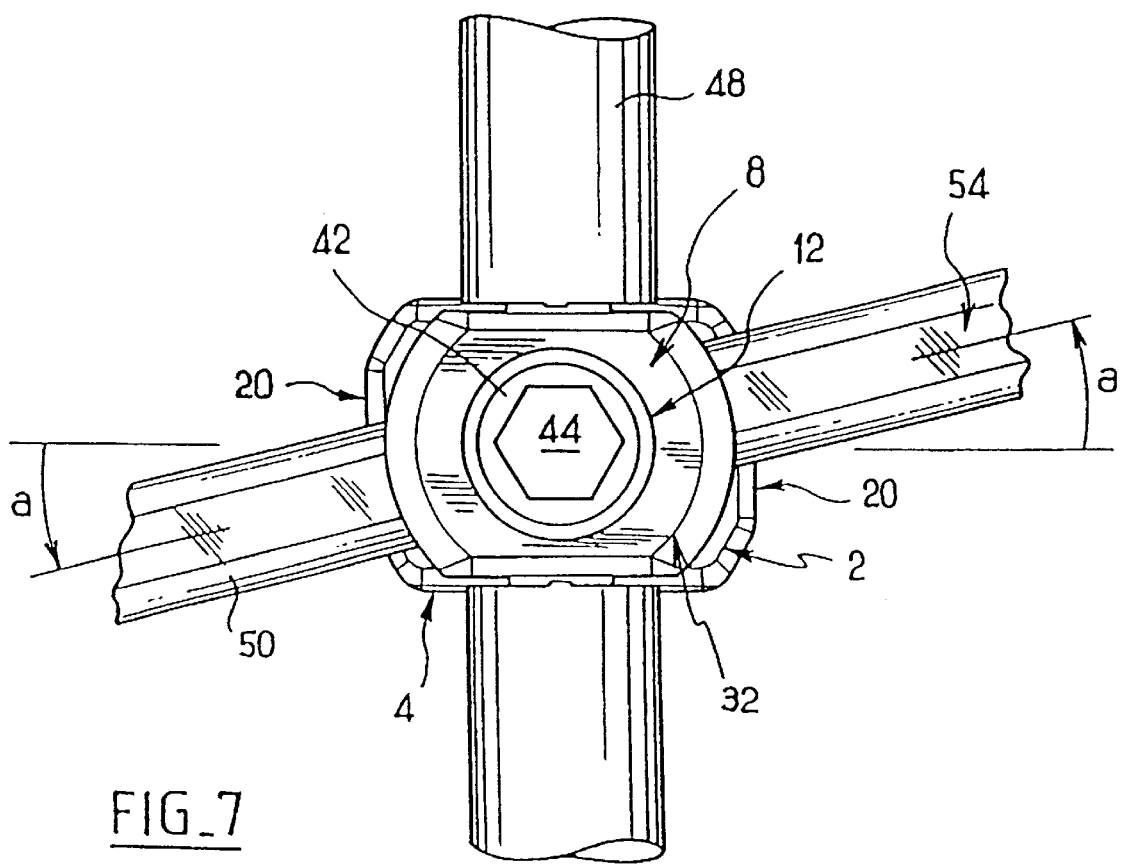
FIG_7

CONNECTOR FOR BACKBONE OSTEOSYNTHESIS DEVICE

The invention relates to osteosynthesis devices.

Document EP-0 778 007-A1 discloses a backbone osteosynthesis device comprising a rod, a cross-member, a connector, a ring, and a nut. The connector has two jaws adapted to clamp on the rod. It has a housing for receiving the cross-member which extends in a direction that is perpendicular to the rod received between the jaws. The connector is threaded to receive the nut. To assemble the device, the jaws are clipped on the rod, then the ring is engaged on the connector so that it bears against the jaws. The cross-member is inserted in the housing. Finally, the nut is tightened onto the connector. The nut applies thrust to the cross-member so that it bears against the ring. By having inclined faces to provide contact between the ring and the jaws, the ring in turn urges the jaws towards each other so as to clamp onto the rod. Such a device makes it possible to connect a longitudinal rod rigidly to a cross-member, and more generally such devices make it possible for common cross-members to unite two longitudinal rods which extend generally in parallel along the spinal column with each of them connected to the spinal column. Nevertheless, that device has a large number of parts. A large number of individual acts are required to install it and it is relatively complicated to mount.

An object of the invention is to provide a device which can be mounted more quickly and more simply.

To achieve this object, the invention provides a connector for a backbone osteosynthesis device, the connector having two jaws and presenting a housing adapted to receive a rod bearing against the jaws, the connector being arranged so that force on the rod received in the housing and acting towards the jaws urges the jaws towards each other, wherein the connector is made as a single piece.

Thus, the osteosynthesis device has a small number of parts. The number of individual assembly operations to be performed prior to the surgical operation or during the surgical operation is thus reduced, and mounting of the device is simplified.

Advantageously, the connector includes at least one junction contiguous with the jaws, the junction being of a width that is smaller than the width of the connector level with the jaws.

The elastic flexibility of the jaws relative to the remainder of the connector is thus increased without any need to give large dimensions to the connector in order to achieve equivalent flexibility.

Advantageously, the junction has a notch extending from the jaws in the opposite direction to the jaws.

This further increases the flexibility of the jaws.

Advantageously, the connector has a head connected to the jaws by the junction, the width of the junction being less than the width of the head.

Thus, if the head is to receive a clamping member, the dimensions of the head can be large so as to make it easier to manufacture.

Advantageously, the connector is arranged in such a manner that the rod received in the housing bears against respective zones of the jaws that are remote from the junction.

Thus, the lever arm exerted by the transverse rod on the jaws is increased, thereby increasing the clamping of said jaws on the longitudinal rod.

Advantageously, the connector is arranged in such a manner that the rod received in the housing bears against respective edges of the jaws that are remote from the junction.

Advantageously, each of the jaws presents a plane face adapted to extend facing the rod received in the housing, said face sloping towards the inside of the connector.

Advantageously, the connector has a threaded face, the housing extending between the jaws and the threaded face.

Advantageously, the threaded face is formed by a duct extending inside the connector.

This prevents the thread from being exposed on the outside and does not give rise to injury to the body suffering arthrodesia.

The invention also provides an osteosynthesis device comprising first and second rods, a threaded member, and a connector having two jaws adapted to clamp onto the first rod, the connector having a threaded face and a housing extending between the jaws and the threaded face and adapted to receive the second rod bearing against the jaws, the connector being arranged so that a force applied by the threaded member co-operating with the threaded face, against the second rod received in the housing towards the jaws urges the jaws towards each other so as to clamp onto the first rod, wherein the connector is made as a single piece.

Advantageously, the jaws are adapted to be clipped onto the first rod.

Advantageously, the jaws are adapted to clamp onto the first rod in the absence of any force being applied to the jaws.

Advantageously, the jaws are configured in such a manner that the first rod projects from the jaws in a radial direction of the first rod when the first rod is received between the jaws.

It is thus pointless to provide a large gap between the rod and the body suffering from arthrodesia. The device can thus be placed very close to the body.

Advantageously, the first rod forms a link between vertebrae along a backbone, and the second rod forms a transverse union between the first rod and another rod forming a link between vertebrae.

Advantageously, the connector is arranged so that the second rod can be received in the housing while occupying a range of angular positions about a direction perpendicular to the first rod.

It is thus possible at will to adapt the relative position of the two rods to the configuration of the device mounted on the patient.

Other characteristics and advantages of the invention appear further from the following description of a preferred embodiment given by way of non-limiting example. In the accompanying drawings:

FIGS. 1 to 3 are respectively a perspective view, an end view, and a side view of a connector of the invention;

FIG. 4 is a perspective view of an osteosynthesis device of the invention in the mounted state, the device having two connectors of FIG. 1;

FIG. 5 is a view on a larger scale showing a portion of FIG. 4; and

FIGS. 6 and 7 are respectively an end view and a plan view of the FIG. 5 device.

With reference to FIGS. 1 to 3, the connector 2 of the present embodiment of the invention is generally in the form of a rectangular parallelepiped having cutouts which are described in greater detail below, and edges that are rounded so as to avoid any risk of injuring the body suffering from arthrodesia.

The connector has two vertical plane faces 4 comprising a front face and a rear face, which faces are substantially parallel and extend continuously over the full height of the connector. The connector also has two horizontal plane faces comprising a top face and a bottom face 8 and 10 that are parallel to each other and substantially perpendicular to the above-mentioned vertical faces 4. The connector has a generally cylindrical duct 12 extending parallel to the front and rear faces 4, halfway between them, and perpendicular to the top and bottom faces 8 and 10 through which it opens out. The connector is axially symmetrical about the axis of the duct 12.

The connector has two slots 14 extending generally parallel to the top and bottom faces 8 and 10 in two side faces 20 of the connector that extend perpendicularly to the front and rear faces 4. Each slot 14 is generally of channel section being defined by a top face 22 parallel to the top face 8 of the connector, a web face 24 parallel to the side faces 20 of the connector, and a bottom face 26 facing the top face 22 and extending perpendicularly to the front and rear faces 4 while being slightly inclined towards the inside of the connector. The angle between the top and bottom faces 22 and 26 of the slot can lie in the range 2° to 10°, for example. The slots 14 co-operate with the duct 12 which extends between them to define a housing 28 for receiving a cross-member, as described below. Furthermore, on either side of the axis of the duct 12, the slots 14 define two junctions 30 between which the duct 12 and the housing 28 extend.

A portion of the connector extending above the junctions 30 forms a head 32. The two side faces 20 on the head 32 are shaped like two sectors of a common cylinder that is coaxial with the duct 12.

The connector has a bottom cylindrical face 34 contiguous with the bottom face 10 of the connector, perpendicular to the duct 12, and halfway between the two side faces 20. Between them, the slots 14 and the cylindrical face 34 define two jaws 36 each connected to the head 32 by the two junctions 30. On each junction 30, the connector has a notch 38 extending away from the jaws 36 towards the head 32.

The diameter of the duct 12 is smaller in the head 32 than in the remainder of the connector. Inside the head 32, the duct 12 has a thread 40.

With reference to FIG. 2, if the word "width" is used to designate the dimension measured perpendicularly to the side faces 20 of the connector, then the width i of the junctions 30 is less than the width t of the head 32 and less than the width c of the connector at the level of the jaws 36.

The osteosynthesis device is described below with reference to FIGS. 4 to 7.

The device has at least two connectors 2 of the kind shown in FIG. 1. It has two screws 42 each adapted to form a screw-nut link by engaging in the duct 12 of the head 32 of a respective connector. Each screw 42 has a hexagonal socket 44 for receiving a hexagonal key for turning the screw 42 received in the duct 12. The device has two rectilinear longitudinal rods 48 for extending along the backbone of a patient, each being fixed to the vertebrae by anchor members that are not shown and that are known per se. The two rods 48 are of circular profile having the same diameter as the cylindrical face 34 between the jaws. The jaws 36 are adapted to make surface-on-surface contact with the rod. The cylindrical faces 34 of the jaws together extend over a circular arc of total extent exceeding 180° and selected as a function of the properties of the material of the connector so as to enable the jaws 36 to be engaged on the rod 48 by being snap-fastened thereon. As represented by dashed lines in FIG. 2, the cylindrical faces 34 of the jaws present a geometrical outline which extends beyond the bottom face 10 of the connector 2. Thus, when the rod 48 is engaged between the jaws 36, the rod projects beyond the jaws in a radial direction of the rod.

Finally, the device has a rectilinear cross-member 50 of generally rectangular section adapted to be received in the housings 28, passing right through the connectors 2.

All of the elements of the device are made of stainless steel that is preferably biocompatible.

The device is mounted as follows.

The connectors 2 are clipped onto the respective longitudinal rods 48. Thereafter the cross-member 50 is engaged in the two housings 28 of the connectors. The screws 42 are inserted into the ducts 12 of the connectors. Once the two rods 48 and the cross-member 50 have been put into a suitable position, each of the screws 42 is tightened.

As can be seen in particular in FIG. 6, a bottom plane face 52 of the cross-member 50 then comes to bear against the jaws 36, coming into contact therewith solely at the edges 54 constituting the intersection between the side face 20 and the sloping bottom face 26 of the slot 14, given the slope of said bottom face 26 towards the inside of the connector.

During tightening, the screw 42 urges the cross-member 50 downwards towards the jaw 36 along the axis of the duct 12 against a plane top face 54 of the rod. This urging is represented by arrow V. This urging V causes the rod 52 to press against the two jaws 36 along their edges 54 in the same directions. The corresponding forces are presented by arrows T. Because of the configuration of the junctions 30, the notches 38, and the elasticity of the material, the jaws 36 pivot relative to the head 32 about an axis 58 parallel to the longitudinal rod 48 and lying in the notches 38. This movement is represented by arrows R. Under such circumstances, the forces T offset from the axis 58 and extending perpendicularly thereto, move the jaws 36 so that they pivot towards each other to clamp onto the longitudinal rod 48.

The housing 28 is configured in such a manner as to allow the cross-member 50 to move through an angle a about the axis of the duct 12 on either side of the direction perpendicular to the rod 48, as shown in FIG. 7. This makes it possible to fix the cross-member 50 in a position that is not exactly perpendicular to the rod 48. The angle a can, for example, lie in the range ±15° on either side of the perpendicular direction, giving a total range of 30°.

Only one pair of connectors 2 and one cross-member 50 are shown associated with the longitudinal rods 48. Nevertheless, the osteosynthesis device advantageously comprises a plurality of pairs of connectors 20 each having a cross-member 50 associated with the same two longitudinal rods 48 along the backbone.

Provision can be made for the jaws 36 to be adapted by the elasticity of the connector material to clamp onto the rod 48 even in the absence of any force being exerted by the cross-member and the screw 42. For this purpose, it suffices to form the jaws so that they naturally take up a position closer to each other than the position they occupy when receiving the rod 48. Nevertheless, the jaws still allow the connector to be moved manually along the rod in order to be repositioned.

Alternatively, provision could be made for the connector 2 to be adapted to slide along the rod 48 in the absence of any clamping by means of the cross-member 50 and the screw 42.

What is claimed is:

1. A connector for a backbone osteosynthesis device, the connector comprising two jaws and a housing adapted to receive a rod bearing against the jaws, the connector being arranged so that force on the rod received in the housing and acting towards the jaws urges the jaws towards each other, wherein the connector is made as a single piece.

2. The connector according to claim 1, including at least one junction contiguous with the jaws, the junction being of a width (i) that is smaller than the width (c) of the connector level with the jaws.

3. The connector according to claim 2, wherein the junction has a notch extending from the jaws in the opposite direction to the jaws.

4. The connector according to claim 2 or 3, further including a head connected to the jaws by the junction, the width (j) of the junction being less than the width (t) of the head.

5. The connector according to claim 2, arranged in such a manner that the rod received in the housing bears against respective zones of the jaws that are remote from the junction.

6. The connector according to claim 5, arranged in such a manner that the rod received in the housing bears against respective edges of the jaws that are remote from the junction.

7. The connector according to claim 6, wherein each of the jaws presents a plane face adapted to extend facing the rod received in the housing, said face sloping towards the inside of the connector.

8. The connector according to claim 1, wherein characterized in that it has a threaded face, the housing extending between the jaws and the threaded face.

9. The connector according to claim 8, characterized in that the threaded face is formed by a duct extending inside the connector.

10. An osteosynthesis device comprising first and second rods, a threaded member, and a connector having two jaws adapted to clamp onto the first rod, the connector having a threaded face and a housing extending between the jaws and the threaded face and adapted to receive the second rod bearing against the jaws, the connector being arranged so that a force (T) applied by the threaded member co-operating with the threaded face, against the second rod received in the housing towards the jaws urges the jaws towards each other so as to clamp onto the first rod, the device being and wherein the connector is made as a single piece.

11. The device according to claim 10, wherein the jaws are adapted to be clipped onto the first rod.

12. The device according to claim 11, wherein the jaws are adapted to clamp onto the first rod in the absence of any force being applied to the jaws.

13. The device according to claim 10, the jaws are configured in such a manner that the first rod projects from the jaws in a radial direction of the first rod when the first rod is received between the jaws.

14. The device according to claim 10, the connector is arranged so that the second rod can be received in the housing while occupying a range of angular positions about a direction perpendicular to the first rod.

15. The device according to claim 10, the first rod forms a link between vertebrae along a backbone, and the second rod forms a transverse union between the first rod and another rod forming a link between vertebrae.

* * * * *

UNITED STATES PATENT AND TRADEMARK OFFICE
CERTIFICATE OF CORRECTION

PATENT NO. : 6,368,320 B1
DATED : April 9, 2002
INVENTOR(S) : Le Couedic et al.

It is certified that error appears in the above-identified patent and that said Letters Patent is hereby corrected as shown below:

Column 3,
Line 41, "i" should read -- j --.

Column 5,
Line 3, "(i)" should read -- (j) --.
Lines 24-25, cancel "wherein characterized in that it has".
Line 24, after "1," insert -- further having --.
Lines 27-28, cancel "characterized in that".
Line 27, after "8," insert -- wherein --.

Column 6,
Line 9, cancel "the" (second occurrence).
Line 10, cancel "device being".
Line 17, after "to" insert -- any one of --.
Line 17, "claim" should read -- claims --.
Line 17, after "10" insert -- to 12, wherein --.
Line 21, after "10," insert -- wherein --.
Line 25, after "10," insert -- wherein --.

Signed and Sealed this

Seventeenth Day of September, 2002

*Attest:*

JAMES E. ROGAN
*Director of the United States Patent and Trademark Office*

*Attesting Officer*